United States Patent [19]

Toth et al.

[11] 4,411,988
[45] Oct. 25, 1983

[54] PROCESS FOR THE DETERMINATION OF ANTI-HYALURONIDASE AND AN AGENT SUITABLE FOR THIS PURPOSE

[75] Inventors: Tibor Toth, Marburg; Reiner Gils, Schwalmstadt, both of Fed. Rep. of Germany

[73] Assignee: Behringwerke A.G., Marburg, Fed. Rep. of Germany

[21] Appl. No.: 342,824

[22] Filed: Jan. 26, 1982

Related U.S. Application Data

[63] Continuation of Ser. No. 139,456, Apr. 11, 1980, abandoned.

[30] Foreign Application Priority Data

Apr. 14, 1979 [DE] Fed. Rep. of Germany ....... 2915309

[51] Int. Cl.³ .............. G01N 33/54; C12Q 1/00; C12Q 1/34; C12Q 1/14
[52] U.S. Cl. .............................. 435/7; 435/4; 435/18; 435/36; 435/810; 436/808; 436/811
[58] Field of Search ........... 435/4, 7, 18, 201, 36, 435/232, 810; 23/230 B; 424/7, 8; 436/531, 532, 533, 534; 636/808, 811

[56] References Cited

U.S. PATENT DOCUMENTS 3,945,889  3/1976  Mima et al. ............... 435/201
4,152,212  5/1979  Pope et al. ................ 435/232
4,373,932  2/1983  Gribnau et al. ............. 435/7

OTHER PUBLICATIONS

Ganguly et al., Indian J. Med. Res. 66, 802–808 (1977).
Knoell, Z. Immun.-Forsch. 142, 276–283 (1971).
Ganguly, et al., "Comparative Evaluation of Antihyaluronidase Antistseptolysin O and Streptozyme Test in Acute Rheumatic Activity", Chem. Absts., vol. 88, No. 9 (1978), p. 248, Abs. No. 60739z.
Tolksdorf, "The in vitro Determination of Ayaluronioase,"Meth. Biochem. Anal., vol. 1 (1954), pp. 425–457.
Greiling, "Hyaluronic Acid", Methods of Enzymatic Analysis, vol. 3 (1974), Acadamic Press, N.Y., pp. 1157–1164.
Greiling, et al., "Chondrohin 4-Sulphate, Chondrohin 6-Sulfate and Dermation Sulphate", Methods of Enzymatic Analysis, vol. 3 (1974), Academic Press, N.Y., pp. 1165–1171.

Primary Examiner—Thomas G. Wiseman
Attorney, Agent, or Firm—Curtis, Morris & Safford

[57] ABSTRACT

A simple rapid assay for the determination of antihyaluronidase and a kit for use therein. The assay is based on the precipitation of unreacted hyaluronic acid by a cationic detergent and acid dyestuff. The assay is preferably performed as a dilution series. The dyestuff reagent contains 1 to 10 parts by weight acid dyestuff to 10 parts by weight of cationic detergent.

4 Claims, No Drawings

PROCESS FOR THE DETERMINATION OF ANTI-HYALURONIDASE AND AN AGENT SUITABLE FOR THIS PURPOSE

This is a continuation of application Ser. No. 139,456, filed Apr. 11, 1980, abandon Mar. 21, 1983.

The invention relates to a process for the determination of anti-hyaluronidase, i.e. antibodies directed against hyaluronidase, and to a diagnostic agent appropriate for this purpose.

Hyaluronidase is an extracellular metabolism product of streptococci of group A according to Lancefild. Hyaluronidase is an antigen which induces the formation of specific antibodies in humans. A knowledge of the antibody concentration in human blood is of importance for making diagnoses.

In the case of rheumatic fever caused by streptococci, an increase of antihyaluronidase is frequently found in the blood of the patients, besides an increase in the antistreptolysin titer. In most cases these values are well in line with each other. However, about 20% of the patients with streptococcal infections of group A do not show a significant increase of the anti-streptolysin-O titer, but do show a markedly increased antihyaluronidase titer. There has therefore been a demand for a diagnostic determination of antihyaluronidase.

A great number of methods for determining antihyaluronidase have already been described, the most important of which are the following:

1. Mucin coagulum reduction test according to Quinn [R. W. Quinn, J. clin. Invest. 27, 463 (1948)];
2. turbidity reduction test according to Faber [V. Faber, Acta path. Microbiol. Scand. 31, 345 (1952)];
3. viscosity reduction test according to Quibell [J. Madinaveitia and T. H. H. Quibell, Biochem. J. 34, 625 (1940)].

The method according to Quinn serves to determine the inhibition of the hyaluronidase which specifically decomposes hyaluronic acids (acid mucopolysaccharides synthetized from N-acetyl glucosamine and glucuronic acid). The presence of antibodies against hyaluronidase is indicated by the neutralization of the inhibition of the hyaluronic acid coagulation which starts at an acid pH value, the inhibition becoming evident in the presence of hyaluronidase.

The turbitity reduction test and the modifications thereof are based on the neutralization of the inhibition of the turbidity of hyaluronic acid by anti-hyaluronidase, the inhibition becoming evident in the presence of hyaluronidase.

According to the viscosity reduction test, the neutralization of the reduction of the viscosity of hyaluronic acid solution by anti-hyaluronidase is measured, the viscosity reduction becoming evident in the presence of hyaluronidase.

These methods involve a series of drawbacks for diagnostic laboratories (cf. Bergmeier, Methoden der enzymatischen Analyse, volume I, page 984).

The mucin coagulum reduction test is little sensitive and requires a large amount of enzyme for executing the test. In microtiter plates the test is not accurate.

The measurement of turbidity is suitable only for purified hyaluronidases and requires a particularly pure substrate. Said measurement must be carried out very carefully with regard to the details and requires a high expenditure with regard to the apparatus involved (photometer).

The results of the viscosimetric process depend on the purity of the substrate; another problem is to be seen in the reduction of the viscosity due to non-enzymatic reactions.

Other methods are too insensitive or require a large amount of enzyme for the execution of the test.

In accordance with the invention, a process has been found which makes it possible to determine the anti-hyaluronidase titer with a high sensitivity and high specificity. Another advantage of the method is to be seen in its rapid performance.

The invention provides a process for the determination of anti-hyaluronidase in aqueous solution, which comprises allowing first a defined amount of streptococcal hyaluronidase to act upon a series-diluted solution, thereafter adding a precipitant-dyestuff complex for precipitation of the hyaluronic acid not decomposed by the streptococcal hyaluronidase and determining the limiting concentration found for the precipitation in this process.

The process is based on the knowledge that the hyaluronic acid not decomposed by hyaluronidase may be precipitated with a precipitant which has previously been dyed, thus forming a colored precipitate which is very visible.

The most important factor in said process is the precipitant-dyestuff complex which consists of a cationic detergent and an acid dyestuff.

Suitable cationic detergents within the framework of the invention are especially those of the group of quaternary ammonium compounds, such as cetyl trimethyl ammonium halide, above all cetyl trimethyl ammonium bromide or chloride. Other cationic detergents precipitating hyaluronic acid are pyridinium compounds, such as cetyl pyridinium halides, above all the chloride. However, preference is given to cetyl trimethyl ammonium bromide.

As dyestuff components, in particular acid and chrome dyestuffs are suitable, especially azo dyestuffs, for example dis-azo dyestuffs, but above all Congo red.

By using dyestuff mixtures, the readability of the precipitation limit may even be improved. For example, if a solution of toluidine blue is used, an orange-red precipitate is obtained on or in a light blue ground shade. However, other dyestuffs, such as methyl green or bromophenol blue may also be employed. Toluidine blue is particularly appropriate for forming a blue ground shade.

The dyestuff reagent of the invention contains the following components in the indicated ratio: from 1 to 10 parts by weight of the acid dyestuff are added to 10 parts by weight of the cationic detergent. The two, or optionally several, components are mixed in an aqueous solution at a temperature of from 20° to 100° C., preferably from 60° to 70° C.

A hyaluronic acid substrate appropriate for the execution of the invention may, for example, be prepared as follows:

1 Part by weight of hyaluronic acid is suspended with 50 to 250 parts by weight of an amino acid, for example glycine or β-alanine, in 1000 ml of water. The mixture is allowed to stand at 0° to 50° C. until the hyaluronic acid has been dissolved completely; thereafter it is filtered and lyophilized. Mannitol or albumin are also suitable as lyophilization additives.

The following process may be carried out, for example, in order to prepare the precipitant-dyestuff complex:

1 Part by weight of cetyl trimethyl ammonium bromide (CTA) and 1 to 2 parts by weight of NaOH are suspended in an Erlenmeyer flask with distilled water and heated with constant agitation to 60° to 70° C. Subsequently the solution is cooled to room temperature and the pH value of the solution is adjusted to 3.5 to 10 with acetic acid. After filtration, from 2 to 10 parts by volume of Congo red solution, optionally from 0.02 to 0.5 part by volume of 0.1 molar toluidine blue solution, and from 20 to 40 parts by volume of distilled water are added to 1 part by volume of the above solution, while stirring.

Another subject of the invention is the preciptant-dyestuff complex as such, which contains 10 parts by weight of a cationic detergent and from 1 to 10 parts by weight, preferably 4 parts by weight, of an acid dyestuff, preferably of quaternary ammonium compounds and dis-azo dyestuffs, above all cetyl trimethyl ammonium halide and the dis-azo dyestuff Congo red, preferably in aqueous solution or in a lyophilized form.

Because of its simplicity, the process of the invention is suitable for series analyses. For this purpose, a so-called test kit is suitably made up which comprises the following reagents:

1. Hyaluronic acid substrate consisting essentially of hyaluronic acid and glycine, dry or in solution (0.35 mg of hyaluronic acid, 50 mg of glycine in 1 ml of distilled water). For the hyaluronic acid substrate, the hyaluronic acids or the salts thereof which are sold in commerce may be used.

2. Streptococcal hyaluronidase, for example an enzyme preparation from the culture filtrate of streptococci of group A prepared according to L. W. Wannamaker and W. Yasmineh, J. exp. Med. 126 (1967) 475.

The solution is ready for use with an activity of from 20 IU/ml to 300 IU/ml, preferably from about 75 to 150 IU/ml. The hyaluronidases available in commerce are hardly suitable for the test, since only those hyaluronidases which are obtained from streptococci show an inhibition of the degradation of hyaluronic acid by anti-hyaluronidase in the blood. Preference is given to streptococcal hyaluronidase from a culture filtrate of streptococci of group A.

3. Dyestuff reagent consisting of the precipitant-dyestuff complex in aqueous solution. According to the preferred embodiment, this is cetyl trimethyl ammonium bromide and Congo red in the ratio of 10 to 4. The complex is present in the aqueous solution in a concentration of from 1 g to 2 g per liter, preferably about 1.4 g/l.

4. Anti-streptococcal-hyaluronidase standard is a human serum with a defined concentration of streptococcal anti-hyaluronidase which yields a titer of 256 with a correct test performance.

The process is preferably carried out in series analyses, with dilution series being prepared of those solutions in which the concentration of anti-hyaluronidase is to be determined. If a serum is used, it is suitably heated to about 56° C. for a short time. By means of this process, unspecific reactions which might lead to a wrong measuring result are avoided. To each dilution of the sample is added a known amount of the hyaluronidase, which reacts with the anti-hyaluronidase. Thereafter the sample is mixed with hyaluronic acid with which there only that hyaluronidase which has not been bound to anti-hyaluronidase can react. The hyaluronic acid which has not been decomposed by hyaluronidase is finally precipitated with the precipitant-dyestuff complex. The respective dilution series are brought into relation with the standard series of the anti-hyaluronidase and the hyaluronic acid.

For executing the reactions, a microtiter plate is particularly suitable, because, besides a series of sera, a standard series for the anti-hyaluronidase as well as corresponding controls for the enzyme and the substrate can be applied thereto side by side.

The following Example illustrates the invention.

EXAMPLE

1. Preparation of the reagents 1.1. Lyophilized hyaluronic acid (1.7 mg) is taken up in 5 ml of distilled water.

1.2. Lyophilized streptococcal hyaluronidase (4.3 mg) is dissolved in 3 ml of distilled water.

1.3. The cetyl trimethyl ammonium bromide-dyestuff complex is an aqueous solution of 5.7 mg of cetyl trimethyl ammonium bromide and 2.1 mg of Congo red in 5 ml of water.

1.4. The anti-streptococcal-hyaluronidase standard serum is a liquid stabilized human serum which yields an antihyaluronidase titer of 300 with a correct test performance. 2. Preparation of the serum dilution series.

1.5. Each serum to be examined is previously kept in a water bath at 56° C. for 30 minutes. For this purpose a dilution of the patient serum of 1:16, i.e. 0.1 ml of serum + 1.5 ml of distilled water, is used.

1.6 The anti-hyaluronidase standard serum is likewise diluted in a ratio of 1:16.

1.7. A test plate having several rows of hollows and a least 8 hollows in one row is labelled to characterize the various serum samples to be tested and the serum dilution to be used.

1.8 35 µl of distilled water are pipetted into each hollow of each row intended for the serum or standard dilution, as well as into the row of the enzyme control. 50 µl of distilled water are filled into the hollow for the substrate control.

1.9. 25 µl of the serum dilution in a ratio of 1:16 are pipetted into the first hollow of the serum rows, and the 1:16 dilution of the standard is filled into another row.

1.10. By means of a microdilution pipette dispensing 25 µl, dilution series are prepared which have a final volume of 25 µl in steps of two, starting with 1:16 to 1:4096.

Test mixture

Each hollow of the dilution series (standard and patient sera) contains at first 25 µl of a serum dilution step.

1.11. To each hollow (except the substrate control) are added 25 µl of streptococcal-hyaluronidase solution with the aid of a micropipette. After mixing with a shaking apparatus, the test plate is covered and allowed to stand for at least 15 minutes at room temperatures.

1.12. Subsequently 25 µl of hyaluronic acid-substrate solution are filled into all hollows (including those for the enzyme and substrate control), mixed thoroughly, and after covering the plate, the mixture is allowed to stand for 20 minutes at 37° C.

1.13. Thereafter 50 µl of cetyl trimethyl ammonium bromide-Congo red complex are pipetted into each hollow and agitated for 30 seconds with a vibration apparatus. Finally the limiting concentration of the precipitation is determined upon visual inspection. If an appropriate microtiter plate has been used for the determination, a short-time centrifugation may also be carried out, which is followed by the reading.

Evaluation

For reading the result, the plates are suitably put onto an opal glass plate which can be lit up from below, or onto a reading mirror. There are noted down those dilution steps for standard and patient sera in which an orange precipitate is still visible.

The anti-hyaluronidase titer is found by multiplying the dilution factor of the patent serum by the anti-hyaluronidase concentration in the standard serum, which shows, for example, the precipitation limit in the titer step of 1:256, and dividing by the dilution factor in the standard serum.

For example, a standard serum, precipitate in the dilution of

1:512, and
a patient serum, precipitate in the dilution of
1:1024, yield $\frac{1024 \times 256}{512} = 512$ as titer of the anti-hyaluronidase in the patient serum.

In a comparative test, in which instead of the above-mentioned dyestuff complex under 1.13 cetyl trimethyl ammonium bromide solution is pipetted into the test mixture, a precipitate can no longer be recognized already in the dilution of 1:16, whereas the precipitant-dyestuff complex makes it possible to detect the precipitate even in a dilution of 1:256.

What is claimed is:

1. A method for determining anti-hyaluronidase in an aqueous solution thereof, which comprises first reacting a defined amount of streptococcal hyaluronidase with a dilution series of said aqueous solution of anti-hyaluronidase, adding a defined amount of hyaluronic acid to said dilution series, and then adding a mixture of 10 parts by weight of cetyl trimethyl ammonium halide with from 1 to 10 parts by weight of a dis-azo dyestuff to said dilution series to precipitate the hyaluronic acid not decomposed by streptococcal hyaluronidase, and determining the limiting concentration for which a precipitate forms.

2. A method as in claim 1 wherein said halide is the bromide or chloride and said dyestuff is Congo red.

3. A test kit for determining anti-hyaluronidase in an aqueous solution thereof, said kit comprising:
   (a) human serum containing a defined concentration of anti-hyaluronidase, for use as a reference standard;
   (b) streptococcal hyaluronidase for addition to said reference standard and the aqueous test solution to be tested for reaction with anti-hyaluronidase present in said standard and test solution.
   (c) a hyaluronic acid substrate consisting of a mixture of hyaluronic acid and glycine for subsequent addition to said reference standard and test solution for reaction with excess unreacted hyaluronidase present therein; and
   (d) a dyestuff reagent comprising 10 parts by weight of a cetyl trimethyl ammonium halide with from 1 to 10 parts by weight of a dis-azo dyestuff for further subsequent addition to said reference standard and test solution for the visually detectable precipitation of excess unreacted hyaluronic acid present therein, wherein (a), (b), (c), and (d) are present in amounts sufficient to perform the method of claim 1.

4. A test kit as in claim 3 wherein said halide is the bromide or chloride and said dyestuff is Congo red.

* * * * *